US00PP32084P2

(12) United States Plant Patent
Nir

(10) Patent No.: US PP32,084 P2
(45) Date of Patent: Aug. 18, 2020

(54) ***CHAMELAUCIUM* PLANT NAMED 'SOLAR'**

(50) Latin Name: *Chamelaucium uncinatum*
Varietal Denomination: SOLAR

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 0 days.

(21) Appl. No.: 16/602,500

(22) Filed: Oct. 17, 2019

(51) Int. Cl.
*A01H 5/02* (2018.01)
*A01H 6/00* (2018.01)

(52) U.S. Cl.
USPC ..... Plt./229

(58) Field of Classification Search
USPC ..... Plt./229
See application file for complete search history.

*Primary Examiner* — Susan McCormick Ewoldt
(74) *Attorney, Agent, or Firm* — Cassandra Bright

(57) ABSTRACT

A new and distinct *Chamelaucium* cultivar named 'SOLAR' is disclosed, characterized by early season blooming, and pink flower color with a dark eye. The new variety is a *Chamelaucium*, normally producing cut flower stems, or as a garden or container plant.

1 Drawing Sheet

Latin name of the genus and species: *Chamelaucium uncinatum.*

Variety denomination: 'SOLAR'.

BACKGROUND OF THE INVENTION

The new *Chamelaucium* cultivar is the product of a planned breeding program conducted by the inventor, Nitzan Nir, in Kfar Hess, Israel. The objective of the breeding program was to produce new *Chamelaucium* varieties for ornamental commercial applications. The new variety was selected as a seedling from the breeding program at a commercial nursery in Kfar Hess, Israel.

The crossing resulting in this new variety was made in January of 2013. The seed parent is the unpatented variety referred to as *Chamelaucium uncinatum* 'Nir'. The pollen parent is the variety referred to as *Chamelaucium uncinatum* 'Rotemwax', U.S. Plant Pat. No. 26,024. The new variety was discovered in March of 2014 by the inventor in a group of seedlings resulting from previously mentioned crossing, in a commercial nursery in Kfar Hess, Israel.

Asexual reproduction of the new cultivar has been performed by terminal vegetative cuttings. This was first performed in December of 2015 at a commercial nursery in Kfar Hess, Israel in and has shown that the unique features of this cultivar are stable and reproduced true to type in at least 4 successive generations.

SUMMARY OF THE INVENTION

The cultivar 'SOLAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SOLAR'. These characteristics in combination distinguish 'SOLAR' as a new and distinct *Chamelaucium* cultivar:

1. Position of flowers on the inflorescence , occurring at axillary and terminal positions.

2. Early season blooming.
3. Pink flower color with a dark eye.

PARENT COMPARISON

Plants of the new cultivar 'SOLAR' are similar to plants of the seed parent in most horticultural characteristics, however, plants of the new cultivar 'SOLAR' differ in the following:

1. The new variety begins blooming earlier than the seed parent.
2. The new variety produces more axillary occurring flowers than the seed parent.

Plants of the new cultivar 'SOLAR' are similar to plants of the pollen parent in most horticultural characteristics, however, plants of the new cultivar 'SOLAR' differ in the following:

1. The new variety begins blooming earlier than the pollen parent.
2. The new variety produces more axillary occurring flowers than the pollen parent.
3. The new variety has pink flowers, while the pollen parent has violet flowers.

COMMERCIAL COMPARISON

Plants of the new cultivar 'SOLAR' are comparable to the variety *Chamelaucium uncinatum* 'Jupiter', U.S. Plant Pat. No. 27,255. The two *Chamelaucium* varieties are similar in most horticultural characteristics; however, the new variety 'SOLAR' differs in the following:

1. The new variety has pink flowers, while this comparator has violet flowers.

BRIEF DESCRIPTION OF THE PHOTOGRAPH

The accompanying photograph in FIG. 1 illustrates in full color a close up of typical flowers and foliage of 'SOLAR' on a mature stem at approximately 1 year of age. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'SOLAR' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum* 'SOLAR'.

Age of plant described: About 2 months old from a rooted cutting.

Typical flowering stems harvested per plant: 40 to 60 during the course of the season.

Vase life of flowers: Two weeks.

PROPAGATION

Time to produce a rooted plantlet: 30 to 60 days at approximately 24° C.

Root description: Split root.

PLANT

Growth habit: Upright plant produces multiple stems from a pinch, or after harvesting stems.

Height: 150 cm.

Plant spread: 80 cm.

Branching characteristics:

Length of primary lateral branches: 60 cm to 90 cm on average.

Diameter of lateral branches: 0.1 cm.

Quantity of primary lateral branches: 40 to 60.

Characteristics of primary lateral branches:

*Diameter.*—0.4 cm, measured at 50 cm from top.

*Texture.*—Smooth.

*Strength.*—Low flexibility.

Internode length: Range from 2 to 3 cm, occasionally 5 cm.

FOLIAGE

Leaf:

*Arrangement.*—Opposite.

*Quantity.*—Approximately 5 leaves, in the 5-10 cm section from the top of the branch.

*Average length.*—1.3 cm.

*Average width.*—0.9 mm.

*Shape of blade.*—Needle.

*Apex.*—Acute.

*Base.*—Truncate.

*Margin.*—Entire.

*Texture.*—Smooth.

*Pubescence.*—None.

*Aspect.*—Straight.

*Color.*—Young foliage, upper side: RHS Green 137C. Young foliage, under side: RHS Green 137C. Mature foliage, upper side: RHS Green 137C. Mature foliage, under side: RHS Green 137C.

*Venation.*—Indistinguishable from foliage.

*Petiole.*—Not present.

FLOWER

Natural flowering season: Autumn in Kfar Hess, Israel.

Days to flowering from rooted cutting: Photoperiodic conditions. No juvenility.

Inflorescence type: Panicle.

Individual flower type: 5 petals, about 1.2 cm in diameter.

Rate of flower opening: About 40 days from bud to fully opened flower.

Persistent or self-cleaning: Self-cleaning.

Lastingness: About 2 weeks in a vase.

Bud:

*Shape.*—Flattish.

*Length.*—0.4 cm.

*Diameter.*—0.3 cm.

*Color.*—Base RHS Yellow-Green 145B, apex Greyed-Orange 166C.

Inflorescence size:

*Diameter.*—10 to 18 cm.

*Length.*—15 to 24 cm.

Flower size:

*Diameter.*—Average 1.2 cm.

*Length.*—Average 0.95 cm.

Corolla:

*Petals.*—Arrangement: Rotate hypanthium. Length: Average 0.4 cm. Diameter: Average 0.55 cm. Texture: Smooth. Apex: Round. Base: Fused.

*Color.*—When opening: Upper surface: RHS Purple 75C. Base Greyed-Purple 187C. Lower surface: RHS Purple 75C. Fully opened: Upper surface: RHS Purple-Violet N80D. Base Greyed-Purple 187C. Lower surface: RHS Purple-Violet N80D. Aging: Upper surface: RHS Red-Purple N74C. Base Greyed-Purple 187C. Lower surface: RHS Red-Purple N74C.

Interior corolla/tube:

*Diameter.*—0.6 cm.

*Length.*—0.31 cm.

*Color.*—When opening: Upper surface: RHS Yellow-Green 152B. Lower surface: RHS Yellow-Green 152B. Fully opened: Upper surface: RHS Grey-Brown N199A. Lower surface: RHS Red 45A. Aging: Upper surface: RHS Greyed-Purple 187A. Lower surface: RHS Greyed-Purple 187A.

Calyx/sepals:

*Quantity per flower.*—5.

*Shape.*—Conic.

*Length.*—0.5 cm.

*Width.*—0.6 cm.

*Margin.*—Smooth.

*Texture.*—Smooth.

*Color.*—RHS Green 137C.

Peduncle: Peduncle consists of the plant stem.

Pedicel:

*Length.*—2.0-3.5 cm.

*Diameter.*—0.07 cm.

*Color.*—RHS Yellow-Green 144A.

Fragrance: None.

REPRODUCTIVE ORGANS

Stamens:

*Number.*—10.

*Filament length.*—1 mm.

*Filament color.*—RHS White 155D.

Anthers:

*Shape*.—Oval.

*Length*.—0.3 mm.

*Width*.—1 mm.

*Color*.—RHS Orange 27D.

Pollen: Not observed.

Pistil:

*Number*.—1.

*Style length*.—0.5 cm.

*Style color*.—RHS White 155D.

*Stigma*.—Shape: Round. Color: RHS Violet 83A.

OTHER CHARACTERISTICS

Seeds and fruits: Single flower produces one fruit. When the fruit is fertile, it will produce 1 seed, occasionally 2 seeds.

Disease/pest resistance: Neither resistance nor susceptibility to the normal diseases and pests of *Chamelaucium* have been observed to date.

Temperature tolerance: From −2° C. to 35° C.

Drought tolerance: Very good tolerance for drought.

What is claimed is:

1. A new and distinct cultivar of *Chamelaucium* plant named 'SOLAR' as herein illustrated and described.

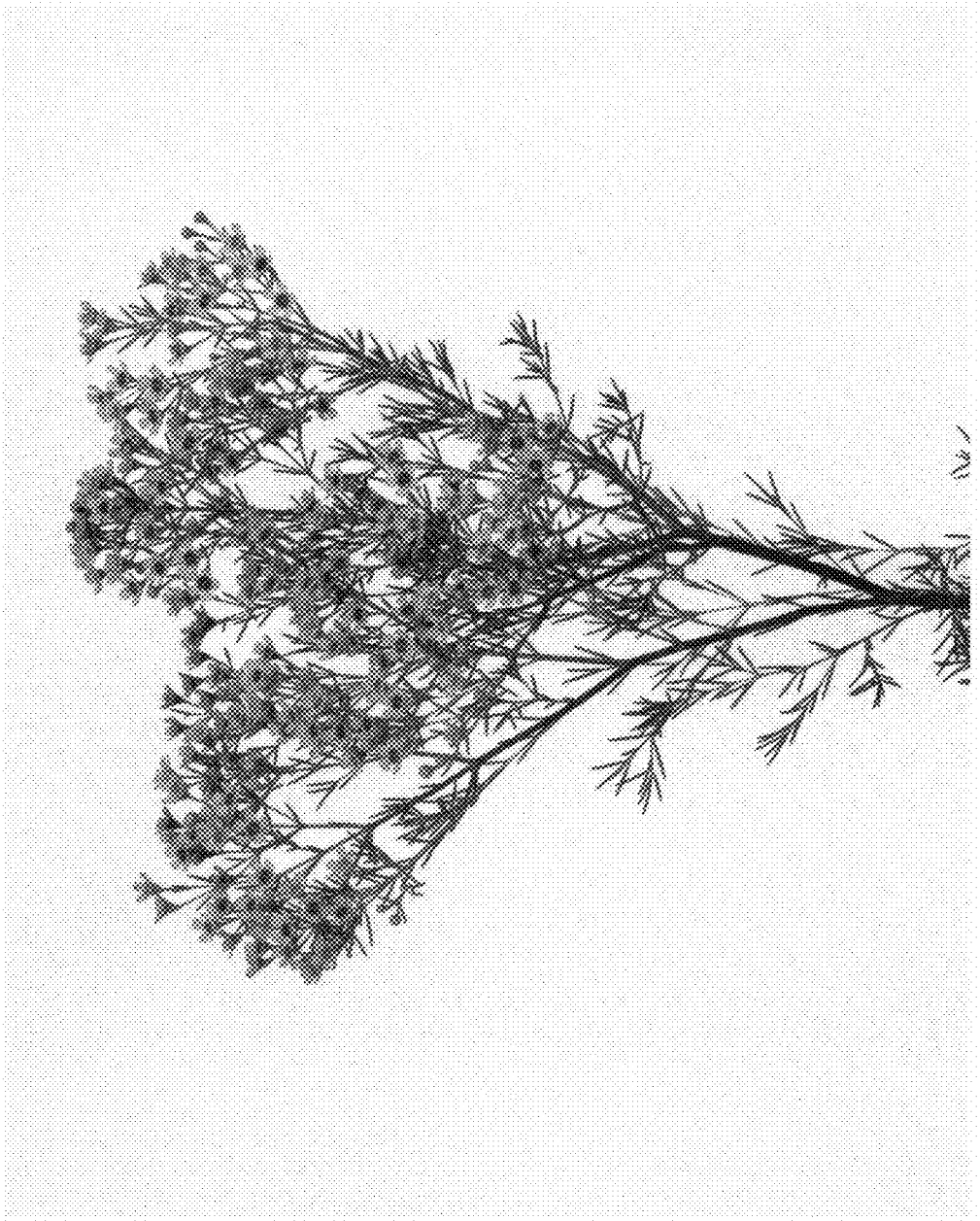

* * * * *